(12) United States Patent
Kalina et al.

(10) Patent No.: US 7,316,707 B2
(45) Date of Patent: Jan. 8, 2008

(54) DEVICE FOR CORRECTING THORACIC SPINE POSITIONING

(76) Inventors: John Kalina, 388 Greenwood Avenue, Ottawa, Ontario (CA) K2B 0X3; Pamela Siekierski, 200 Rideau Terrace, Apt. 406, Ottawa, Ontario (CA) K1M 0Z3; Richard Cuthbertson, 31 Shandon Avenue, Nepean, Ontario (CA) K2J 4E3

(*) Notice: Subject to any disclaimer, the term of this patent is extended or adjusted under 35 U.S.C. 154(b) by 450 days.

(21) Appl. No.: 10/733,347

(22) Filed: Dec. 12, 2003

(65) Prior Publication Data

US 2005/0131462 A1 Jun. 16, 2005

(51) Int. Cl.
*A61H 1/00* (2006.01)

(52) U.S. Cl. ............... 606/240; 606/241; 128/845; 5/632

(58) Field of Classification Search ........... 606/240, 606/241; 601/15; 602/19; 128/845, 846; 5/630, 632, 636
See application file for complete search history.

(56) References Cited

U.S. PATENT DOCUMENTS

| | | | | |
|---|---|---|---|---|
| 4,572,578 | A | * | 2/1986 | Perkins .............. 297/452.32 |
| 5,033,137 | A | * | 7/1991 | Pedrow ................. 5/636 |
| 5,105,489 | A | * | 4/1992 | Meyer ................... 5/652 |
| 5,429,585 | A | * | 7/1995 | Liang .................. 601/15 |
| 2003/0159698 | A1 | * | 8/2003 | Porterfield ........... 128/845 |

* cited by examiner

*Primary Examiner*—Quang D. Thanh

(57) ABSTRACT

Inflammation of the muscles of the posterior thoracic spine can lead to a number of physical ailments. This inflammation can have a number of causes, one typical cause being overuse in a work environment leading to stress or tension within these muscles. Although many related physical ailments can be treated with medication and a properly prescribed and maintained exercise program, at present, an effective, simple-to-use and inexpensive means for correcting the position of the thoracic spine is not available. Embodiments of the present invention provides a resilient pad that is adapted to be interposed between the upper thoracic spine of a user and a substantially hard surface.

1 Claim, 5 Drawing Sheets

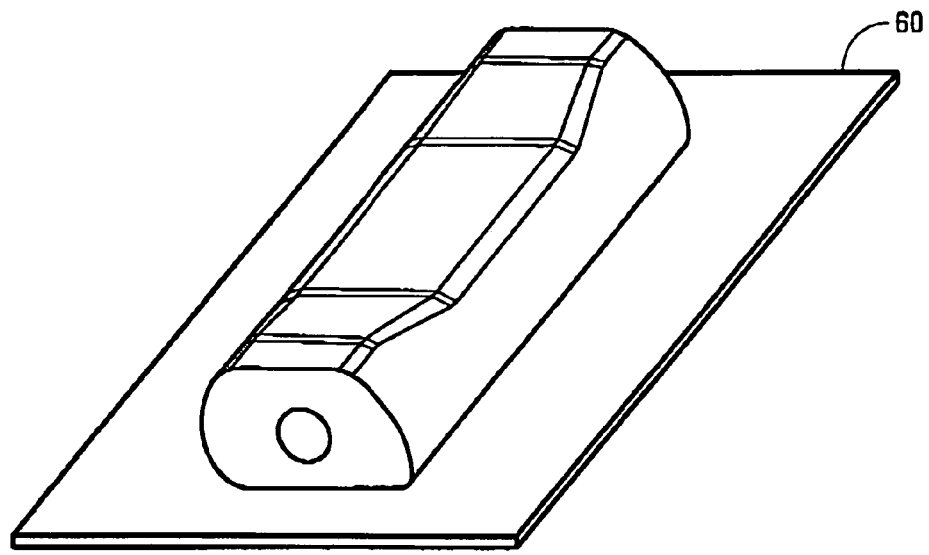
FIG. 7
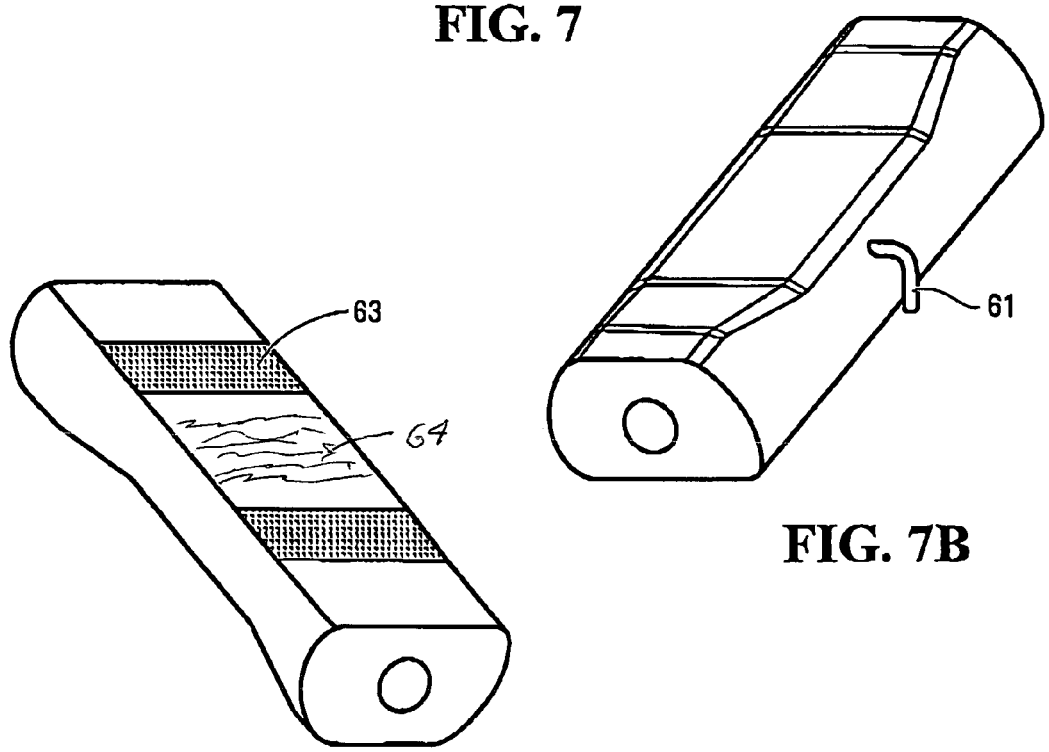
FIG. 7A
FIG. 7B

DEVICE FOR CORRECTING THORACIC SPINE POSITIONING

FIELD OF THE INVENTION

This invention relates to therapeutic devices and in particular therapeutic devices for the correction of thoracic spine positioning.

BACKGROUND

Inflammation of the muscles of the posterior thoracic spine can lead to a number of physical ailments. These ailments can include tension headaches, neck pain, upper back pain, lower back pain, as well as poor posture which can lead to other problems such as premature osteoarthritis of the facet joints of both the thoracic and lumbar spines and premature degeneration of discs.

Inflammation of the muscles of the posterior thoracic spine can have a number of causes, one typical cause being the overuse of these muscles in a work environment, for example, sitting at a desk too long, leading to stress or tension within these muscles.

Although many of the above-mentioned ailments can be treated with medication and a properly prescribed and maintained exercise program, the effectiveness of such remedial measures can be enhanced by correcting the position of the thoracic spine, thereby relaxing the muscles attached thereto.

At present, an effective, simple-to-use and inexpensive means for correcting the position of the thoracic spine is not available.

SUMMARY OF THE INVENTION

In a broad aspect, the present invention provides a resilient pad that is adapted to be interposed between the upper thoracic spine of a user and a substantially hard surface. The length of the pad should correspond approximately to the length of the upper thoracic spine of the user, the portion of the spine located between the user's shoulder blades, typically consisting of thoracic vertebral bodies T1 through T7 or T8. The width of the pad should correspond, approximately to the width of the vertebrae contained within the upper thoracic spine of the user. The thickness of the pad should be sufficient to produce a mild hyper-extension of the user's upper thoracic spine when it is pressed against the pad and the pad is supported by the substantially hard surface.

According to a second aspect of the present invention, the surface of the pad that is adapted to be adjacent to the upper thoracic spine of the user has a asymmetrical V-shaped profile compensating for the changing anatomical structure of the spine as it evolves from the top of the upper thoracic spine toward the bottom of the upper thoracic spine. This may be done by providing a pad wherein both a top end and a bottom end of the pad are of equal thickness and the pad has an asymmetrical V-shaped profile when viewed from the side that tapers downwardly from the top end of the pad at about 10 degrees and downwardly from a point near the bottom end of the pad at about 40 degrees. The latter downward tapering, being inward of the bottom end of the pad, creates a protrusion at its bottom end.

According to a third aspect of the present invention, the surface of the pad that is adapted to be adjacent to the upper thoracic spine of the user has an end-view profile compensating for the structure of the spinal processes of the upper thoracic vertebrae. This may be done by providing a pad having a longitudinal groove extending from the top of the pad to the bottom of the pad.

According to a fourth aspect of the present invention, the upper surface of the pad that is adapted to be adjacent to the upper thoracic spine of the user has a symmetrical U-shaped profile when viewed from the side that forces the upper thoracic spine into a hyper-extended position by providing pressure against spinous processes of the vertebrae. This may be done by providing a pad wherein both a top end and a bottom end of the pad are of equal thickness. The upper surface of the pad at the top end and the bottom end is flat until a point near the top end and a point near the bottom end where the upper surface begins tapering downwardly at about a 10 degree angle to a point from the top end where the tapering stops and to a point from the bottom end where the tapering stops. Between the point from the top end where the tapering stops and the point from the bottom end where the tapering stops is a horizontal depression.

In end cross-section, the surface of the pad that is adapted to be adjacent to the user's upper thoracic spine is preferably of a width wide enough to support a complete vertebral body. Additionally, the surface of the pad that is adapted to be adjacent to the upper thoracic spine may be narrower than the opposite surface. Other cross-sectional shapes will be obvious to persons skilled in the art.

Further refinements may be adapted to the present invention so as to provide additional therapeutic results. These further refinements include means to heat the pad, cool the pad and/or to impart vibratory motion to the pad. Similarly, the pad is easily adapted to receive a magnetic insert so as to additionally provide for magnetic therapy. These may be done by providing a further aspect to the present invention, wherein the pad includes an internal cavity, preferably extending from the top of the pad to the bottom of the pad. The internal cavity may be adapted to receive a tube containing, for example, a gel to heat or cool the pad, or a device capable of imparting a vibratory motion to the pad or a magnetic insert.

The subject-matter of the present invention may be further refined to be adapted to be attached to a board which may be made of the same resilient material as the pad and which acts as a substantially hard surface when such a hard surface is not available.

Further refinements to the present invention include a pad being adapted to be attached to, or formed as an integral part of a chair back, a table, a car seat, another therapeutic device such as an Obus® form, or any other object that is obvious to persons skilled in the art.

Further refinements to the present invention include a pad having straps to affix the pad to a chair, a table, a car seat, a therapeutic device, or any other object that is obvious to persons skilled in the art.

Further refinements to the present invention include a pad having Velcro® to affix the pad to a chair, a car seat, a therapeutic device, or any other object that is obvious to persons skilled in the art.

In use, all embodiments of the present invention are positioned such that an upper thoracic portion thereof is interposed behind the upper thoracic spine of the user and a substantially hard surface. The user then presses against the pad to cause a hyper-extension of the vertebrae causing relaxation of the muscles of the posterior thoracic spine. The user may lay or lean against the pad exerting pressure to the pad for a period of fifteen to twenty minutes per usage, three to four times per day. These time periods are merely suggestive and will depend on each user's individual situation.

BRIEF DESCRIPTION OF THE DRAWINGS

Preferred embodiments of the present invention will now be described with reference to the attached drawings in which:

FIG. 7 is a perspective view of the device shown in FIG. 5 in connection with a board;

FIG. 7(a) is a perspective view of the device shown in FIG. 5 bearing adhesives; and FIG. 7(b) is a perspective view of the device shown in FIG. 5 bearing attachments.

DETAILED DESCRIPTION OF THE PREFERRED EMBODIMENTS

Figure 1:
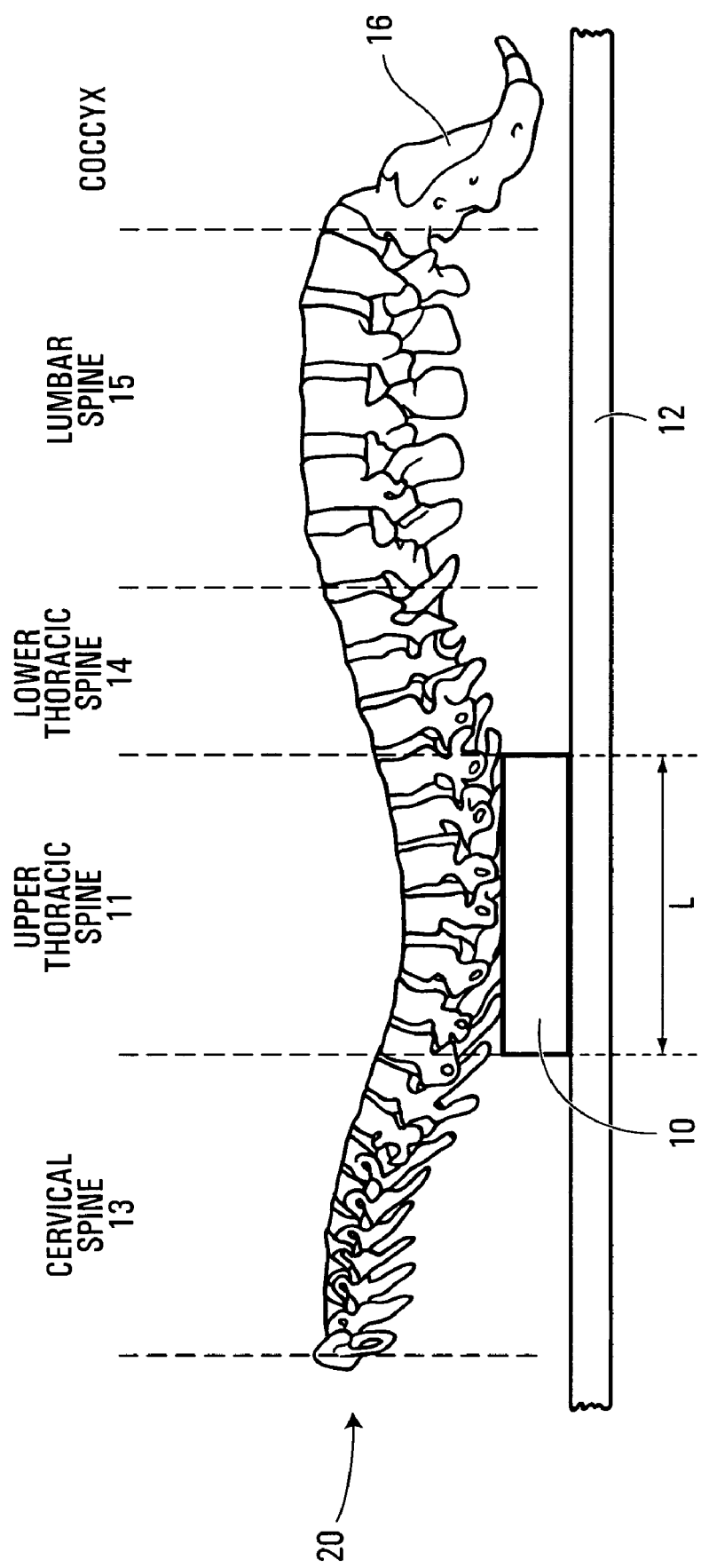
FIG. 1 is a side view of the device according to an embodiment of the present invention, shown interposed between the upper thoracic spine of a user and a substantially hard surface.

FIG. 1 shows a pad (10) according to an embodiment of the present invention, interposed between the user's upper thoracic spine (11) and a substantially hard surface (12). As seen in FIG. 1, the user is generally depicted at (20). FIG. 1 also depicts the user's cervical spine (13), lower thoracic spine (14), lumbar spine (15), and coccyx (16).

The pad (10) is formed from a suitable resilient material such as closed cell polyethylene foam, polystyrene (polymerized) or medical grade glycerin gel. The length (L) of the pad preferably corresponds to the length of the user's upper thoracic spine (11), typically about 7½ inches. The width (W) of the pad (10) preferably corresponds to the width of the vertebrae contained in the user's upper thoracic spine (11), typically about 2¾ inches. The thickness (T) of the pad should be sufficient to produce a mild hyper-extension of the user's upper thoracic spine (11) when the user's upper thoracic spine is pressed against the pad (10) as the pad is supported by a substantially hard surface (12). If the pad (10) is formed of the above-mentioned resilient materials, the thickness will be about 1 ¾ inches.

The width of the pad ensures that the width of the vertebrae is supported by the resilient material of the pad as the upper thoracic spine is hyper-extended. The length of the pad ensures that no individual vertebra is manipulated as the user applies pressure to the pad by pressing against it with his or her upper thoracic spine.

Figure 3:
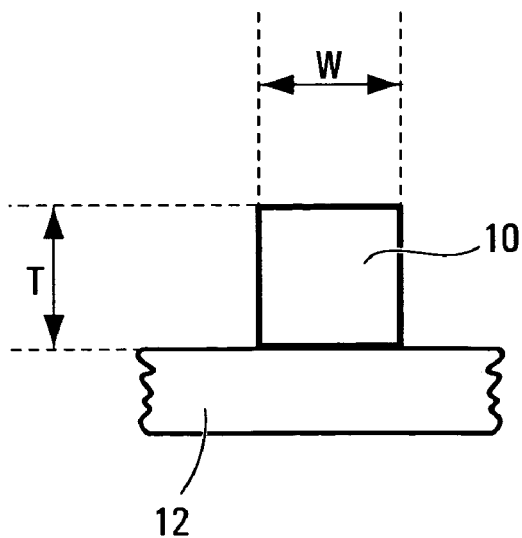
FIG. 3 is an end view of the device shown in FIG. 1.
Figure 6:
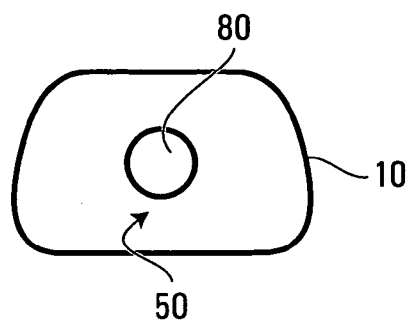
FIG. 6 is an end view of the device shown in FIG. 5.

As well as having a rectangular cross-section as shown in FIG. 3, the pad (10) may have an upper surface that is narrower than the lower surface as depicted in FIG. 6 in association with another embodiment of the invention. In such a tapered pad (10), the upper surface of the pad (10) will have a width approximately equal to the width of the vertebrae of the upper thoracic spine (11).

Figure 2:
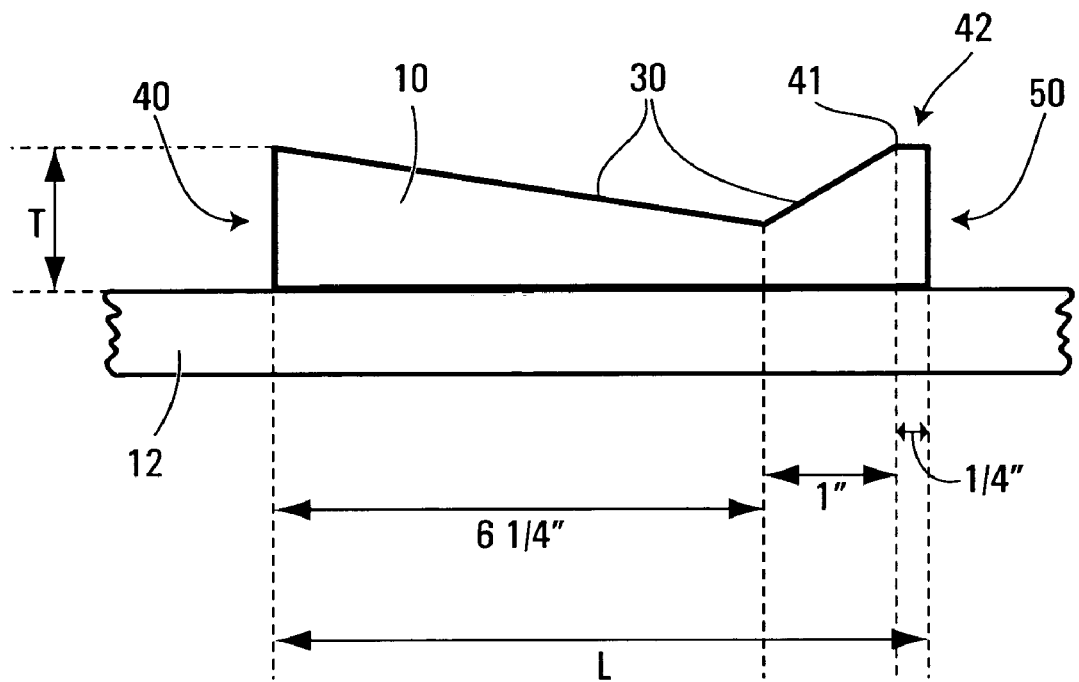
FIG. 2 is a side view of a second embodiment of the device of the present invention.

FIG. 2 depicts a second embodiment of the present invention in which the upper surface (30) of the pad (10) has an asymmetrical V-shaped profile when viewed from the side that tapers downwardly from a top end (40) toward a bottom end (50) at about a 10 degree angle and also tapers downwardly from a point (41) near the bottom end (50) toward the top end (40) at about a 40 degree angle. In the case of a pad (10) that is 7½ inches long, the base of the asymmetrical V will be about 6¾ inches from the top end (40) and 1¼ inches from the bottom end (50). Because the point (41) from which the 40 degree angle tapering commences is removed from the bottom end (50), a protrusion (42) is created at the bottom end of pad (10).

In the case of the pad (10) of the second embodiment to the present invention illustrated in FIG. 2, the asymmetric V-shaped profile of the upper surface tends to force the upper thoracic spine into a more ergonomically anatomically sound position. The protrusion (42) found at the bottom end (50) of the pad (10) allows for the anatomical transitions that occur as upper thoracic vertebrae begin to transform into the more robust heavier vertebral bodies found in the lower thoracic spine (14) and the lumbar spine (15).

Figure 4:
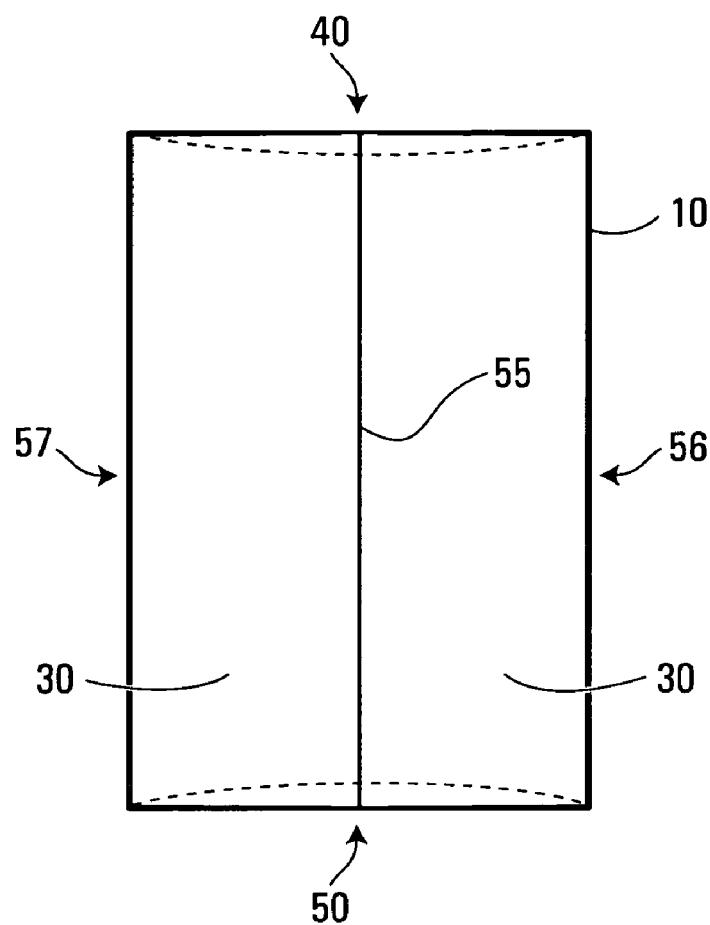
FIG. 4 is a front view of a third embodiment of the device of the present invention.
Figure 4A:
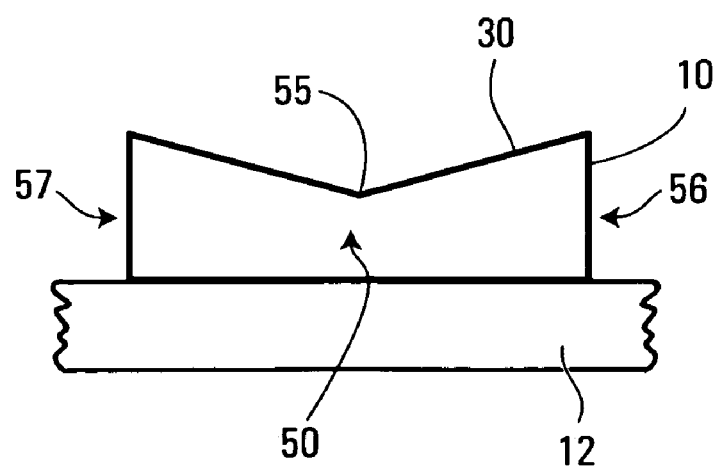
FIG. 4(a) is an end view of the device shown in FIG. 4.

FIGS. 4 and 4(a) depict a third embodiment of the present invention in which the upper surface (30) of the pad (10) has a longitudinal groove (55) extending from the top of the pad (40) to the bottom of the pad (50). The longitudinal groove (55) is equidistant between a right end of the pad (56) and a left end of the pad (57). When the pad (10) is positioned between the user's upper thoracic spine (11) and a substantially hard surface (12), the groove (55) is positioned to cradle the spinal processes of the vertebrae of the upper thoracic spine (11) when the user is applying pressure to the pad (10).

Figure 5:
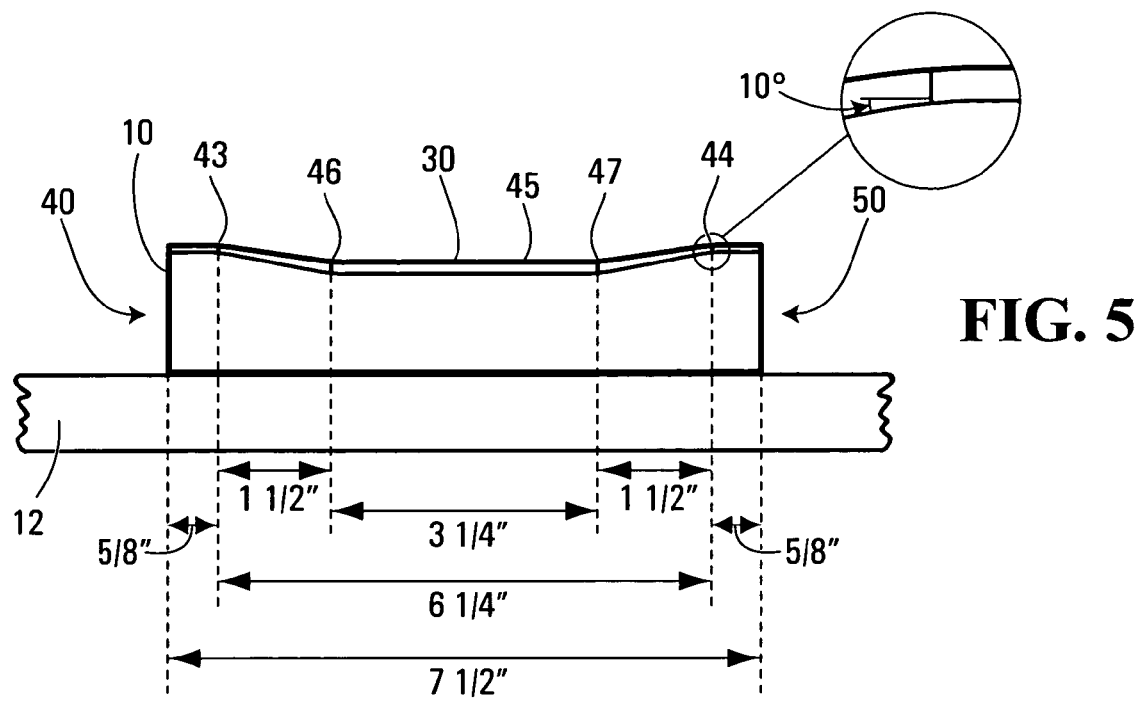
FIG. 5 is a side view of a fourth embodiment of the device of the present invention.
Figure 5A:
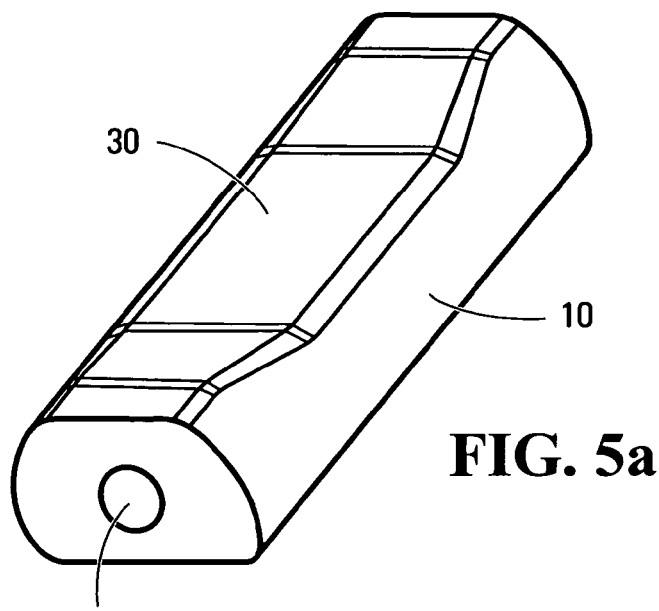
FIG. 5(a) is a perspective view of the device shown in FIG. 5.

FIGS. 5 and 5(a) depict a fourth embodiment of the present invention in which the upper surface (30) of the pad (10) has a symmetrical U-shaped profile when viewed from the side. A top end (40) of the pad (10) and a bottom end (50) of the pad (10) are of equal thickness. The top end (40) and the bottom end (50) are flat until a point near the top end (43) and a point near the bottom end (44) where the upper surface (30) begins tapering downwardly, at about a 10 degree angle, to a point from the top end where the tapering stops (46) and to a point from the bottom end where the tapering stops (47). Between the point from the top end where the tapering stops (46) and the point from the bottom end where the tapering stops (47) is a horizontal depression (45). In the case of a pad (10) that is 7½ inches long, the base of the symmetrical U will be about 6¼ inches wherein the downward tapering at about a 10 degree angle from the point near the top end (43) extends for about 1½ inches to a point from the top end where the tapering stops (46), the downward tapering at about a 10 degree angle from the point near the bottom end (44) extends for about 1½ inches to a point from the bottom end where the tapering stops (47) and the horizontal depression that occurs between the point from the top end where the tapering stops (46) and the point from the bottom end where the tapering stops (47) is 3¼ inches.

In the case of the pad (10) of the fourth embodiment to the present invention illustrated in FIG. 2, the symmetrical U-shaped profile of the upper surface, following the contours of the upper thoracic spine (11) more closely, tends to force the upper thoracic spine (11) into a hyper-extended position.

FIGS. 5 and 6 depict a refinement to the embodiments of the present invention illustrated in FIGS. 1, 2, 4 and 5(a), the pad having a cavity (80) extending from the top end (40) of the pad (10) to the bottom end (50) of the pad. The cavity (80) is adapted to receive a tube containing, for example, gel to heat or cool the pad (10), a device capable of imparting a vibratory motion to the pad (10) or a magnetic insert. A tube containing gel to heat or cool the pad (10) or a device capable of imparting a vibratory motion to the pad (10) or a magnetic insert may be used in combination with the pad in order to supplement or increase the therapeutic relief provided by the pad (10) alone.

To use the device that is the subject of the present invention, a user (20) lies or leans against a substantially hard surface (12), either horizontally or vertically, with the pad (10) located under the user's upper thoracic spine as depicted in FIG. 1. The weight of the user's body on the pad (10) and the substantially hard surface (12) results in the pad pushing the upper thoracic spine (11) of the user (20) upward relative to both the remainder of the user's spine as well as the muscles connected to the upper thoracic spine (11). Thus, the pad (10) produces a mild hyper-extension of the upper thoracic spine (11), which in turn allows for certain muscles located in the upper thoracic spinal area, for example, the posterior postural thoracic spinal muscles, to relax by actively bringing the muscle origins and insertions on bony prominences together. This hyper-extension also alleviates the tension found at intra-vertebral and para-spinal muscles.

When used correctly, all embodiments of the present invention put the upper thoracic vertebral bodies (thoracic one, T1, through to thoracic seven, T7 or thoracic eight, T8) into a mild anatomically hyper-extended position. This hyper-extension alleviates muscular strain on postural muscles of the posterior upper thoracic spine (11) by physically pulling the postural muscles together. With the origins and insertions of the muscles being pulled together the muscle bellies are placed in a relaxed position thereby relieving the stress that has been placed upon them through overuse.

As depicted in FIGS. 7, 7(a) and 7(b), where there is no substantially hard surface (12) available to the user (20), a further embodiment of the pad (10) has the pad (10) used in combination with a board (60) that may or may not be made of the same resilient material as the pad (10). Further embodiments of the present invention may have the pad (10) being affixed to or integral with therapeutic devices for back relief such as an Obus® form or other similar products, or a seatback of a vehicle (a car or truck seat), or a chair or a table. This may be done by having a pad (10) that is physically built into a therapeutic device or the seat of a vehicle or a chair or a table. Alternatively, a pad (10) may be provided with attachment means such as straps (61), for example elastic straps, that are capable of being tightly affixed to a therapeutic device, a seat of a vehicle, a chair or a table or another object wherein the affixing of the pad (10) to these objects results in the pad (10) being immobile and wherein the therapeutic device, the seat of the vehicle, the chair, the table or the other object serve as the substantially hard surface. Alternatively, a pad may be affixed to therapeutic devices, a seat of a vehicle or a chair by Velcro® (63) or adhesive means (64) wherein the pad (10) is provided with such adhesive material on the lower surface of the pad (10).

Although various embodiments of the pad (10) have been described as having specific dimensions, it is to be understood that the present invention also contemplates a pad having any dimensions that serve the same object and function as those described above, in the manner described above.

Although a first embodiment of the pad (10) has been described as having a rectangular cross-section when viewed from the end, it is to be understood that other cross-sections are contemplated, such as U-shapes, oval shapes and circular shapes, for example.

Although a third embodiment of the pad has been described as having a longitudinal groove (55) being equidistant from the right end (56) and the left end (57) of the pad (10), it is to be understood that the longitudinal groove (55) need not be equidistant from the right end (56) and the left end (57) of the pad (10), but may also be located at any other position that serves the same purpose as that described above.

Although the pad (10) may have a cavity that has been described as extending through the entire inner surface of the pad, it is to be understood that the cavity may extend only through a portion of the inner surface of the pad.

Although the pad (10) may have a cavity that has been described as adapted to receiving a tube containing gel to heat or cool the pad, it is to be understood that the cavity may be adapted to receive other means for heating and cooling the pad other than tubes containing gel.

Numerous modifications and variations of the present invention are possible in light of the above teachings. It is therefore to be understood that within the scope of the appended claims, the invention may be practiced otherwise than as specifically described herein.

The invention claimed is:

1. A pad for therapeutic correction of thoracic spine positioning in a patient, said pad having a length, a width, a thickness, a top end, a bottom end, and an upper surface, said length of said pad being substantially a length of an upper thoracic spine of the patient, said width of said pad being substantially a width of vertebrae of the upper thoracic spine of the patient, said thickness of said pad being sufficient to induce a mild hyper-extension of the upper thoracic spine of the patient when said pad is positioned between the upper thoracic spine of the patient and a substantially hard surface and when the upper thoracic spine of the patient is pressed against said pad, said top end and said bottom end of said pad being of substantially equal thickness, said upper surface of said pad lies adjacent the upper thoracic spine in use and has a side-view profile shaped to accommodate a contour of the patient's spine as the contour evolves from a top end of the upper thoracic spine toward a bottom end of the upper thoracic spine and said upper surface has a symmetrical U-shaped side-view profile that tapers downwardly from a first point near said top end of said pad to a second point some distance from said top end where the tapering stops and that tapers downwardly from a third point near said bottom end of said pad to a fourth point some distance from said bottom end where the tapering stops, wherein between the second and fourth points is a horizontal depression, and wherein the tapering from the first point to the second point and the tapering from the third point to the fourth point are each at about 10 degrees.

* * * * *